(12) United States Patent
Khandoker

(10) Patent No.: US 11,207,214 B2
(45) Date of Patent: Dec. 28, 2021

(54) LUMINANT SAFETY EYEWEAR

(71) Applicant: Junayet Khandoker, West Jordan, UT (US)

(72) Inventor: Junayet Khandoker, West Jordan, UT (US)

(*) Notice: Subject to any disclaimer, the term of this patent is extended or adjusted under 35 U.S.C. 154(b) by 0 days.

(21) Appl. No.: 16/442,774

(22) Filed: Jun. 17, 2019

(65) Prior Publication Data

US 2021/0330503 A1    Oct. 28, 2021

Related U.S. Application Data

(60) Provisional application No. 62/685,984, filed on Jun. 16, 2018.

(51) Int. Cl.
| | | |
|---|---|---|
| *F21V 33/00* | (2006.01) | |
| *A61F 9/02* | (2006.01) | |
| *F21V 5/00* | (2018.01) | |
| *F21V 9/08* | (2018.01) | |
| *F21Y 115/10* | (2016.01) | |

(52) U.S. Cl.
CPC .............. *A61F 9/029* (2013.01); *F21V 5/006* (2013.01); *F21V 9/083* (2013.01); *F21V 33/0004* (2013.01); *F21Y 2115/10* (2016.08)

(58) Field of Classification Search
CPC ... F21V 9/08; F21V 9/083; F21V 9/40; F21V 33/0004; F21V 33/0008
See application file for complete search history.

(56) References Cited

U.S. PATENT DOCUMENTS 10,620,460 B2 *  4/2020  Carabin .............. F21V 23/0471

\* cited by examiner

*Primary Examiner* — Sean P Gramling
(74) *Attorney, Agent, or Firm* — Dobbin IP Law, P.C.; Geoffrey E. Dobbin

(57) ABSTRACT

A luminant safety eyewear device with improved lighting may feature a central light source with color changing lenses. The lenses may be manually or electromagnetically manipulated into position. Three lenses may be provided to change color emitted from white, to red, to green and/or blue. Alternately, multiple light sources or a color-changing light source may be utilized either with or without multiple lenses.

16 Claims, 6 Drawing Sheets

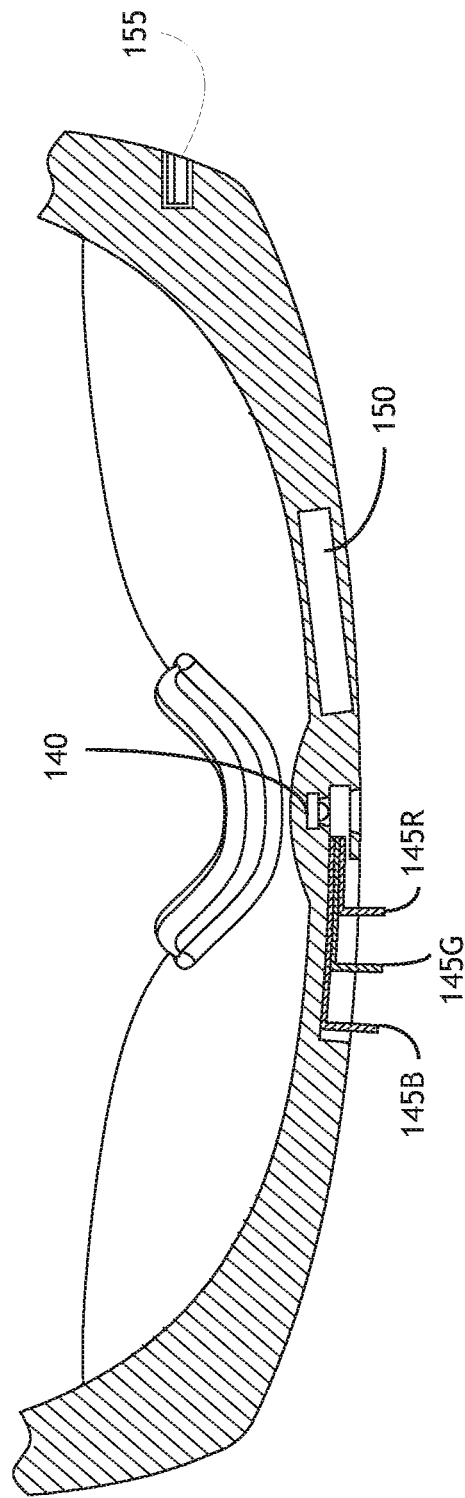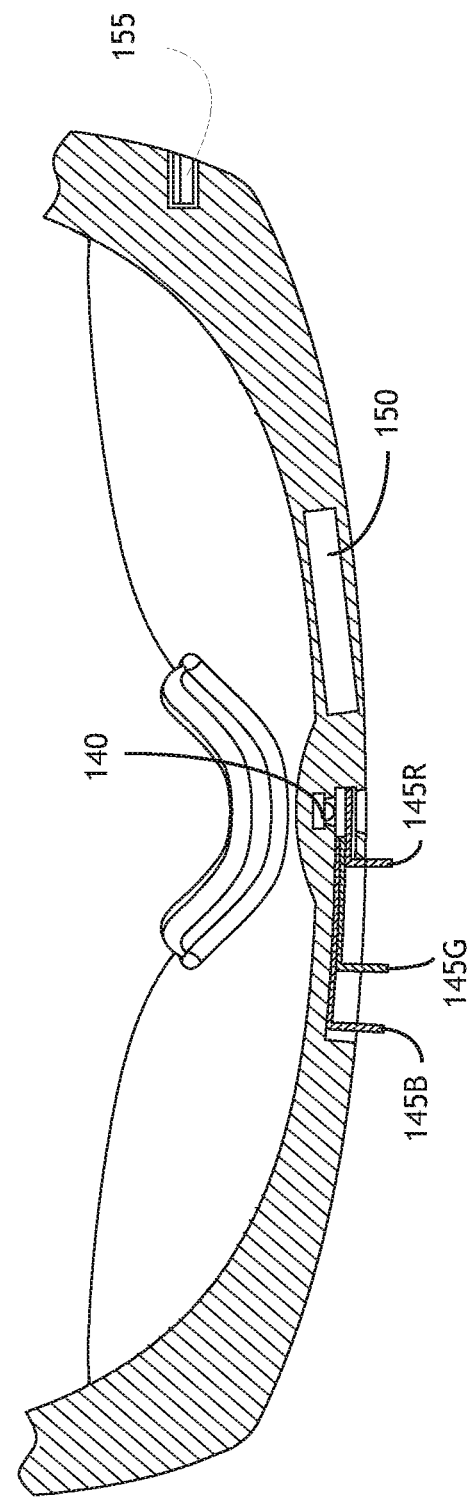
FIG. 3A
FIG. 3B

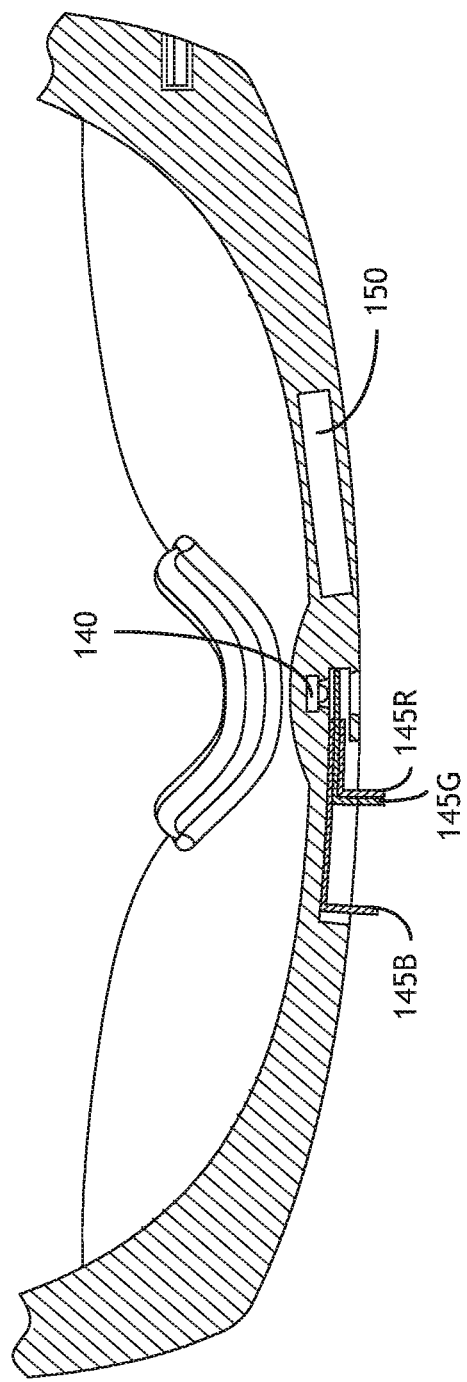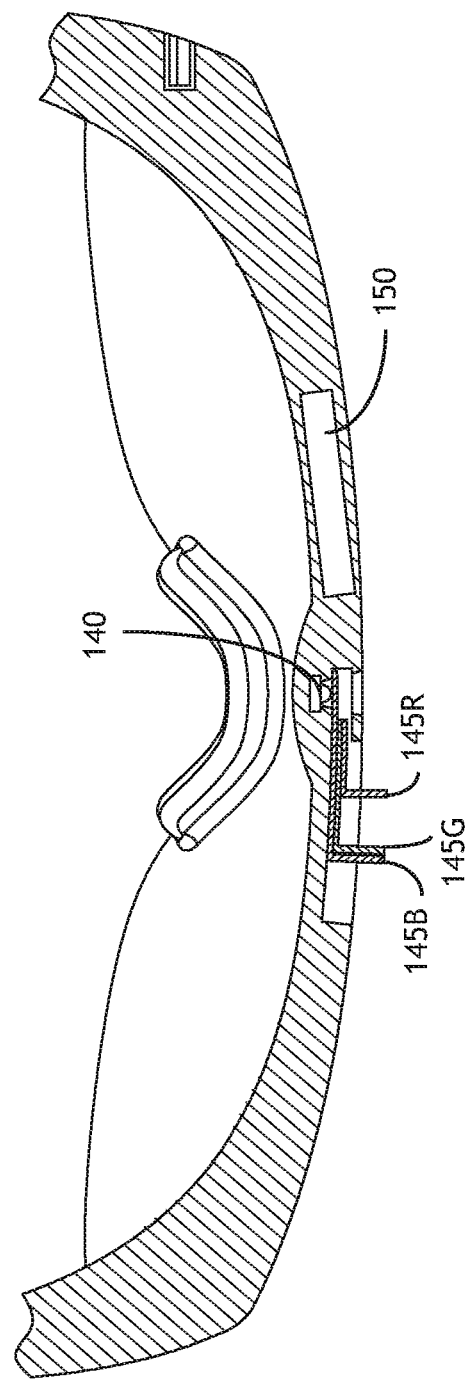

LUMINANT SAFETY EYEWEAR

CROSS-REFERENCES TO RELATED APPLICATION

This application claims priority as a non-provisional perfection under 35 U.S.C. 119 (e)(3) of prior filed U.S. Application 62/685,984, filed Jun. 16, 2018, and incorporates the same by reference in its entirety herein.

FIELD OF THE INVENTION

The present invention relates to the field of safety equipment and more particularly relates to a set of safety eyewear with an incorporated lighting source and color filters for the same.

BACKGROUND OF THE INVENTION

Safety is a paramount concern in many industries. As such there are many different devices which are designed for different levels of protection for different parts of the human body. The eyes are no exception. Safety eyewear are well known in the art and come in many different forms. One need of those using such eyewear is often to keep one's hands free as they are working. This often includes some source of illumination. Many stands, holders, braces, etc. have been developed for this purpose. However, the addition of a light source to the eyewear allows a person to have one less object to manually manipulate and places the light exactly where it is needed.

The present invention is a pair of safety eyewear with a centrally mounted light source and a plurality of light filters associated with the same. The filters may be moved over the light source by either manual or electromechanical means.

The present invention represents a departure from the prior art in that the safety eyewear of the present invention allows for a centrally mounted light source with color change capabilities.

SUMMARY OF THE INVENTION

In view of the foregoing disadvantages inherent in the known types of safety eyewear, an improved luminant safety eyewear device may provide safety eyewear that meets the following objectives: easily worn and charged, effective in providing light to where a user needed while also allowing a color change feature for use in individual specialized lighting needs. As such, a new and improved Luminant safety eyewear may comprise an eyewear body encompassing a light source and power source for the same while also including at least one light filter movable over said light source in order to accomplish these objectives.

The more important features of the invention have thus been outlined in order that the more detailed description that follows may be better understood and in order that the present contribution to the art may better be appreciated. Additional features of the invention will be described hereinafter and will form the subject matter of the claims that follow.

Many objects of this invention will appear from the following description and appended claims, reference being made to the accompanying drawings forming a part of this specification wherein like reference characters designate corresponding parts in the several views.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also, it is to be understood that the phraseology and terminology employed herein are for description and should not be regarded as limiting.

As such, those skilled in the art will appreciate that the conception, upon which this disclosure is based, may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 3A is a sectional view of the luminant safety eyewear of FIG. 2, taken alone line 3-3, with all lenses stowed.

FIG. 3B is a sectional view of the luminant safety eyewear of FIG. 2, taken alone line 3-3, with a red lens deployed.

FIG. 3C is a sectional view of the luminant safety eyewear of FIG. 2, taken alone line 3-3, with a green lens deployed.

FIG. 3D is a sectional view of the luminant safety eyewear of FIG. 2, taken alone line 3-3, with a blue lens deployed.

DETAILED DESCRIPTION OF THE PREFERRED EMBODIMENT

With reference now to the drawings, a preferred embodiment of the luminant safety eyewear is herein described. It should be noted that the articles "a", "an", and "the", as used in this specification, include plural referents unless the content clearly dictates otherwise.

Figure 1:
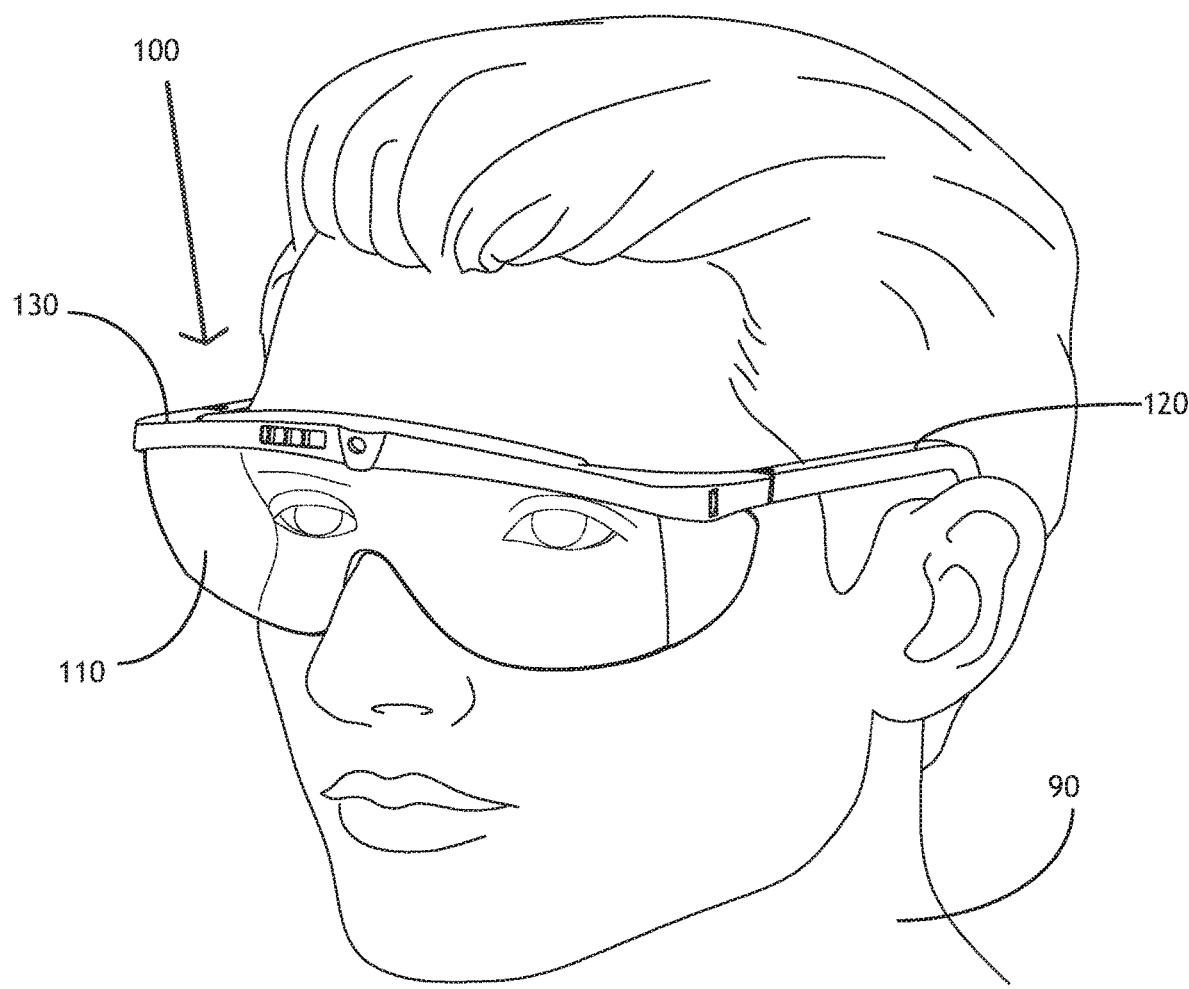
FIG. 1 is a perspective view of an individual wearing a pair of Luminant safety eyewear according to the present invention.
Figure 2:
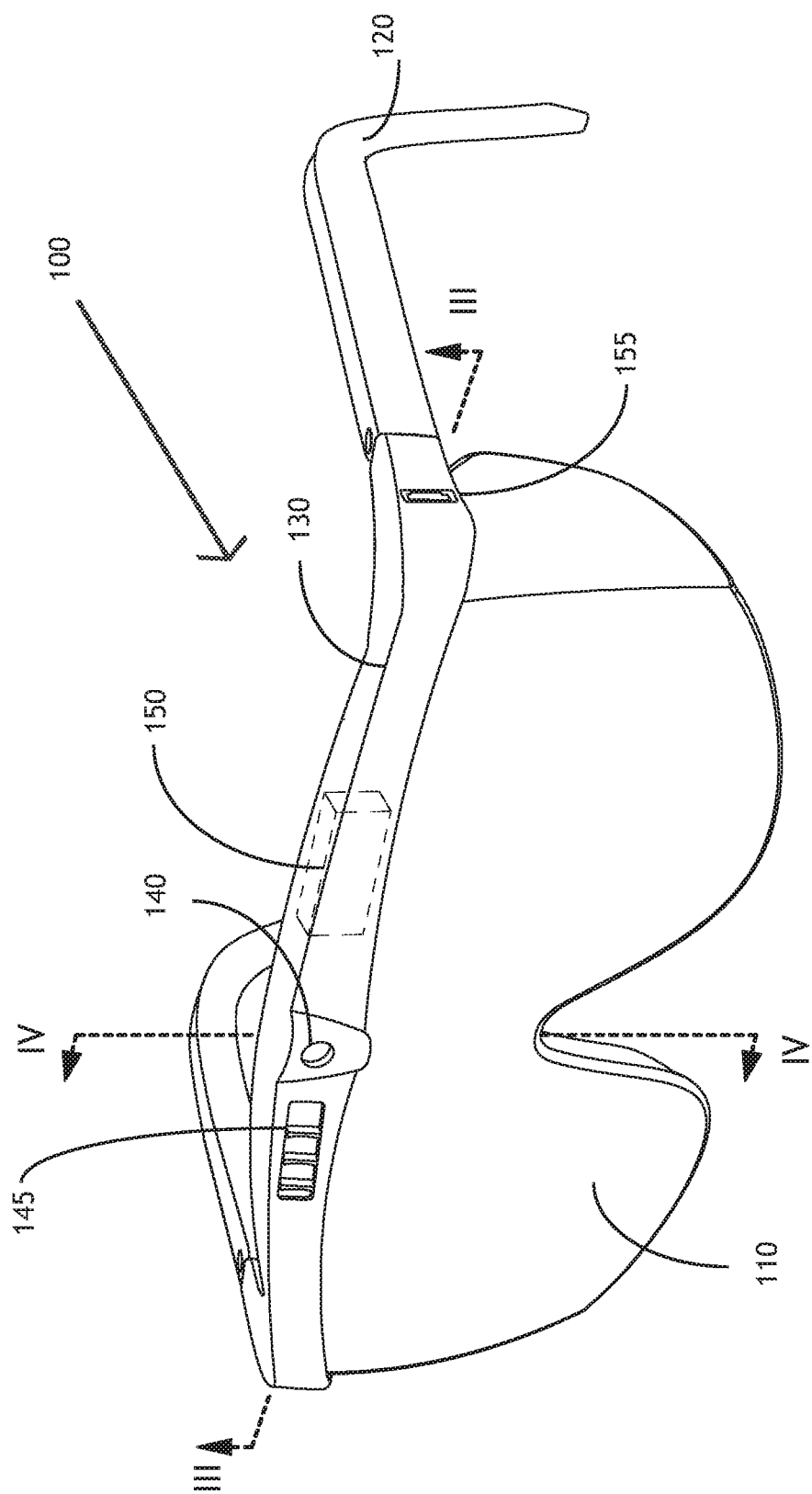
FIG. 2 is a perspective view of the luminant safety eyewear of FIG. 1.

With reference to FIG. 1, a user 90 may place the eyewear 100 over the face, covering eyes with lenses 110 and with earpieces 120 over the ears. A support frame 130 supports both earpieces 120 and lenses 110. It also supports a light source 140 over the bridge of the frame, a power source for the same 150 and at least one colored filter or lens 145 (FIG. 2). In preferred embodiments, a plurality of colored filters may be utilized, stacked one behind the other, to one side of the light source 140.

Figure 4:
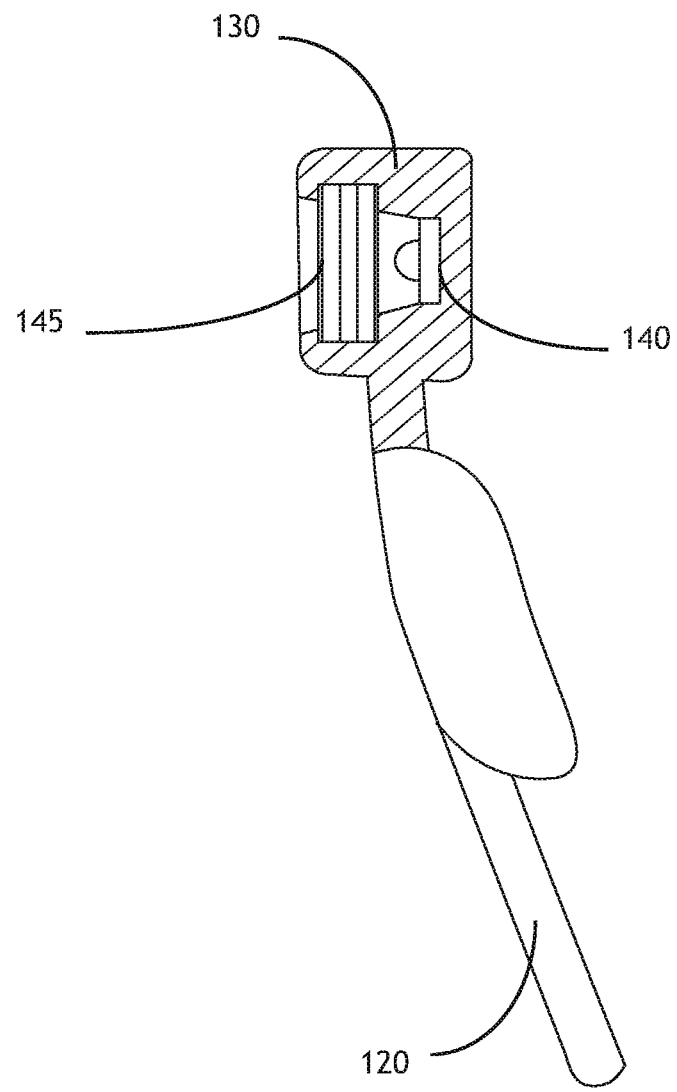
FIG. 4 is a sectional view of the luminant safety eyewear of FIG. 2, taken along line 4-4.

One embodiment, shown in FIGS. 2-4, the lenses 145R, 145G, 145B, nest to the right side of the light source 140 while a rechargeable battery resides to the left. Lenses may be any color, with preference for red, green, and blue. White may be achieved by having a base white light source 140. A charging port 155 is provided on the support frame 130. Each lens may be generally "L" shaped, with the short leg extending outward. The short leg allows the user to slide one lens or another over the light source 140, as is the illustrated in FIGS. 3B, 3C, and 3D and returned to a stowage position at will.

Figure 5:
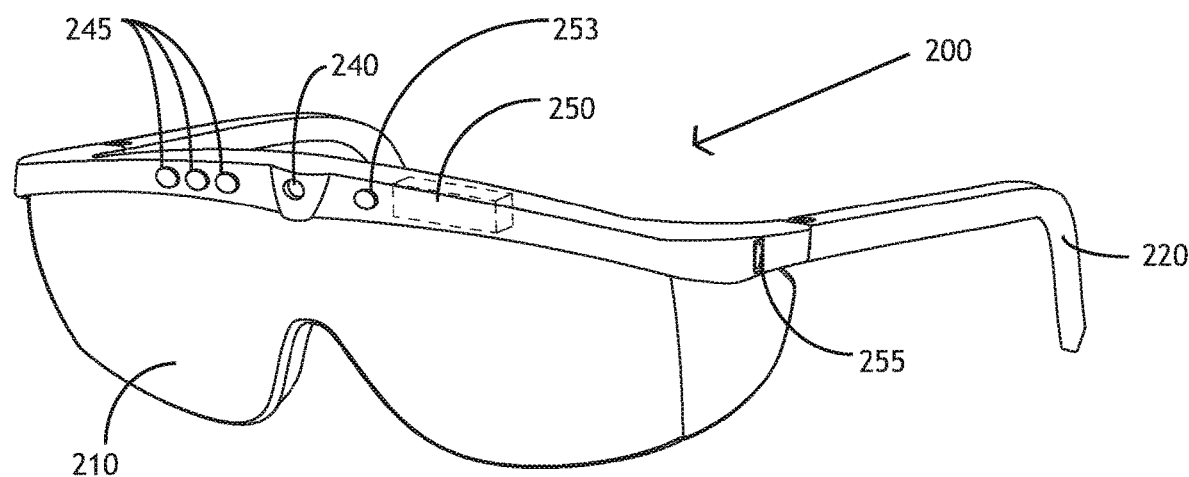
FIG. 5 is a perspective view of an alternate embodiment of luminant safety eyewear, with electromagnetic actuators moving the lenses.
Figure 6:
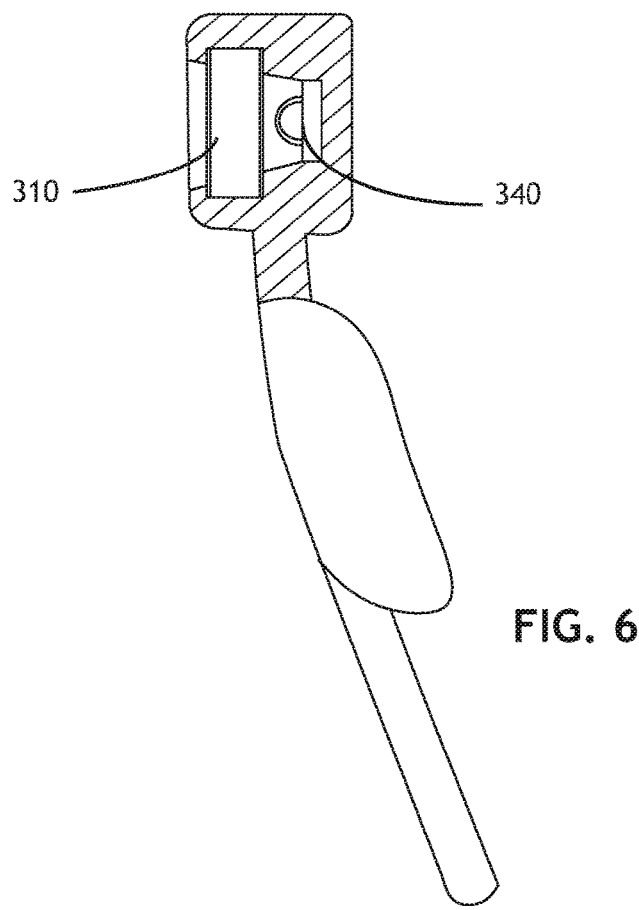
FIG. 6 is a sectional view of an alternate embodiment of luminant safety eyewear in the same section as FIG. 4.

Filters may also be any suitable material, such as glass or plastic. In an alternate embodiment 200, shown in FIG. 5, the lenses may be moved by an actuator system, with push buttons 245 controlling the system. A single power button 253 may not only turn on/off the power to the light source 240, but also may retract the lenses. The light source may be any suitable light source, such as one LED chip capable of emitting different electromagnetic wavelengths or multiple LED chips 340 (FIG. 6) which may emit different spectra of electromagnetic radiation and may include visible light, IR, or UV radiation. The light source 340 may be controlled by a similar switch bank as the one shown in FIG. 5. A single lens 310 may be provided to help protect the LED or LEDs or multiple lenses, as has been already described in this specification, may be utilized to create different lighting effects.

Although the present invention has been described with reference to preferred embodiments, numerous modifications and variations can be made and still the result will come within the scope of the invention. No limitation with respect to the specific embodiments disclosed herein is intended or should be inferred.

What is claimed is:

1. A luminant safety eyewear apparatus comprising:
    a frame, earpieces, and safety lenses, with a bridge located in the frame between the safety lenses;
    a central light source located over the bridge of the frame;
    a rechargeable power source for the light source; and
    at least one colored lens movable over the light source and stowed when not in use by sliding into the frame.

2. The luminant safety eyewear of claim 1, the at least one colored lens being three such lenses, nested over each other when stowed.

3. The luminant safety eyewear of claim 2, the lenses being manually manipulated.

4. The luminant safety eyewear of claim 2, the lenses being electromechanically actuated.

5. A luminant safety eyewear apparatus comprising:
    a frame, earpieces, and safety lenses;
    a central light source located over a bridge of the frame, said light source selectively emitting different wavelengths of light;
    a rechargeable power source for the light source;
    at least one lens located proximate the central light source, said at least one lens being movable over said light source and stowed when not in use by sliding into the frame; and,
    a control switch.

6. The luminant safety eyewear of claim 5, the at least one lens being three such colored lenses, nested over each other when stowed.

7. The luminant safety eyewear of claim 5, the at least one lens being manually manipulated.

8. The luminant safety eyewear of claim 5, the at least one lens being electromechanically actuated.

9. The luminant safety eyewear of claim 5, the central light source being a plurality of LED chips.

10. The luminant safety eyewear of claim 9, each LED chip of the plurality of LED chips being capable of emitting different wavelengths of electromagnetic radiation.

11. A luminant safety eyewear apparatus comprising:
    a frame, earpieces, and safety lenses, with a bridge located in the frame between the safety lenses;
    a central light source located over the bridge of the frame;
    a power source for the light source; and
    at least one colored lens movable over the light source and stowed when not in use by sliding into the frame.

12. The luminant safety eyewear of claim 11, the at least one colored lens being three such lenses, nested over each other when stowed.

13. The luminant safety eyewear of claim 12, the lenses being manually manipulated.

14. The luminant safety eyewear of claim 12, the lenses being electromechanically actuated.

15. The luminant safety eyewear of claim 11, the central light source being a plurality of LED chips.

16. The luminant safety eyewear of claim 15, each LED chip of the plurality of LED chips being capable of emitting different wavelengths of electromagnetic radiation.

* * * * *